(12) United States Patent
Metz-Stavenhagen

(10) Patent No.: US 7,766,944 B2
(45) Date of Patent: Aug. 3, 2010

(54) ANCHORING ELEMENT FOR FASTENING A ROD OF A DEVICE FOR ADJUSTING A HUMAN OR ANIMAL VERTEBRAL COLUMN ON A VERTEBRA

(76) Inventor: Peter Metz-Stavenhagen, Schlossstrasse 24, Bad Wildungen (DE) 34537

( * ) Notice: Subject to any disclaimer, the term of this patent is extended or adjusted under 35 U.S.C. 154(b) by 0 days.

(21) Appl. No.: 10/515,046

(22) PCT Filed: May 19, 2003

(86) PCT No.: PCT/DE03/01609

§ 371 (c)(1),
(2), (4) Date: Oct. 19, 2005

(87) PCT Pub. No.: WO03/096915

PCT Pub. Date: Nov. 27, 2003

(65) Prior Publication Data

US 2006/0155277 A1 Jul. 13, 2006

(30) Foreign Application Priority Data

May 21, 2002 (DE) ............................ 202 07 851 U

(51) Int. Cl.
*A61B 17/70* (2006.01)
(52) U.S. Cl. ..................................................... 606/266
(58) Field of Classification Search .................. 606/61, 606/70, 71, 72, 73
See application file for complete search history.

(56) References Cited

U.S. PATENT DOCUMENTS

| | | | |
|---|---|---|---|
| 5,190,543 A | 3/1993 | Schlaepfer | |
| 5,330,474 A * | 7/1994 | Lin | 606/61 |
| 5,487,744 A * | 1/1996 | Howland | 606/61 |
| 5,591,166 A | 1/1997 | Bernhardt et al. | |
| 5,879,350 A | 3/1999 | Sherman et al. | |
| 5,882,350 A * | 3/1999 | Ralph et al. | 606/61 |
| 6,379,357 B1 * | 4/2002 | Bernstein et al. | 606/61 |
| 6,565,567 B1 * | 5/2003 | Haider | 606/61 |
| 6,716,214 B1 * | 4/2004 | Jackson | 606/61 |
| 6,733,502 B2 * | 5/2004 | Altarac et al. | 606/61 |

FOREIGN PATENT DOCUMENTS

| | | |
|---|---|---|
| DE | 39 23 996 C2 | 1/1991 |
| DE | 100 05 385 A1 | 8/2001 |
| EP | 0 885 598 A2 | 12/1998 |
| EP | 1 090 595 A2 | 4/2001 |
| WO | WO 98/25534 A1 | 6/1998 |

\* cited by examiner

*Primary Examiner*—Thomas C Barrett
*Assistant Examiner*—Nicholas Woodall
(74) *Attorney, Agent, or Firm*—Thomas R. Vigil

(57) ABSTRACT

An anchoring element for fastening a rod of a device for adjusting a human vertebral column on a vertebra and having a retainer for receiving the rod, a securing element attachable on the retainer and acting against the rod, a fastening element for attachment to the vertebral body and a clamping device between the retainer and the fastening element including a ring-shaped mount, a partially spherical bearing and an intermediate element embedded in the mount and surrounding the bearing. The bearing comprises level guiding surfaces on opposite sides. The intermediate element has mating counter surfaces which enable the retainer to move in one axial direction only relative to the fastening element and the level counter surfaces are formed on an inner side of one of two generally circumferentially extending elongate segments of the intermediate element.

6 Claims, 3 Drawing Sheets

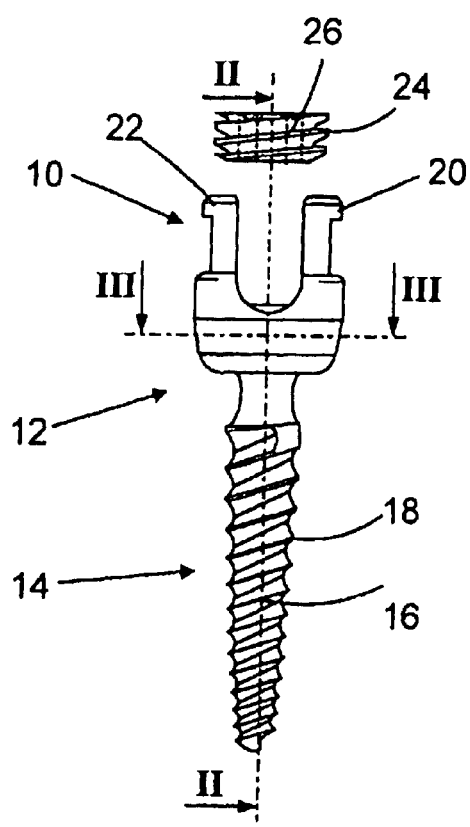
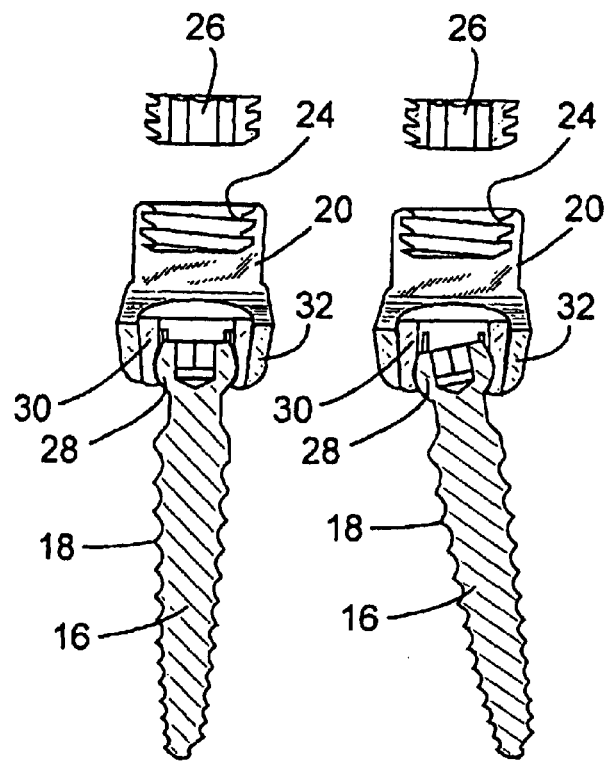
Fig. 1   Fig. 2a   Fig. 2b
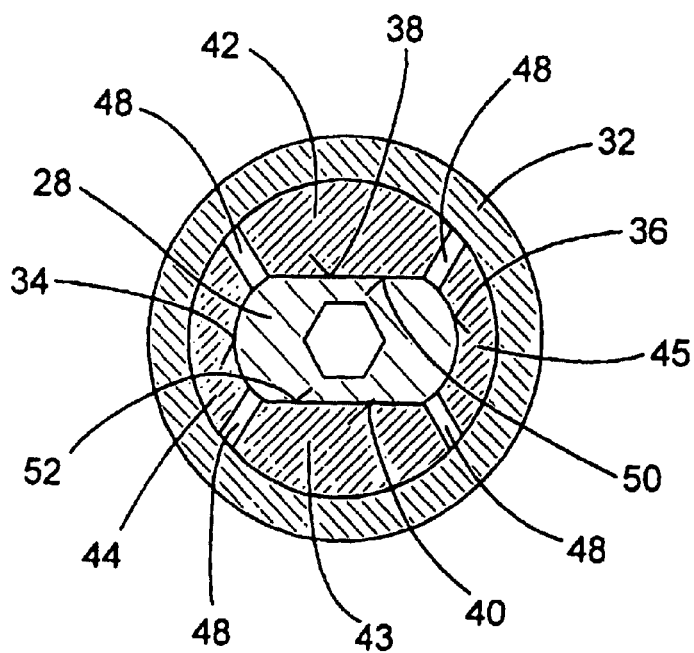
Fig.3

ANCHORING ELEMENT FOR FASTENING A ROD OF A DEVICE FOR ADJUSTING A HUMAN OR ANIMAL VERTEBRAL COLUMN ON A VERTEBRA

CROSS-REFERENCE TO RELATED APPLICATION

This application claims Priority from German Application No. DE 202 07 851.5 filed on 21 May 2002

BACKGROUND OF THE INVENTION

1. Field of the Invention

The present invention relates to an anchoring element for fastening a rod of a device for adjusting a human or animal vertebral column on a vertebra, said anchoring element having a retaining means for receiving the rod, a securing element that is attachable on the retaining means and acting against the rod, a fastening element for attachment to the vertebral body and a clamping device which is arranged between the retaining means and the fastening element, including a ring-shaped mount, a bearing having partially the shape of a spherical segment and an intermediate element embedded in the mount and surrounding the bearing, the mount being free to move relative to the bearing when in its released state whilst the mount is clampingly retained on the bearing through the intermediate element when in its clamped state and the mount being rigidly connected to the retaining means and the bearing to the fastening element.

2. Description of the Prior Art

An anchoring element having the features mentioned herein above and implemented as a pedicle screw is known from EP 0 885 598 A2. The fastening element is thereby implemented as a threaded shaft having a bearing formed at the head end thereof. Said bearing is integrally connected with the threaded shaft and is configured in the shape of a sphere in the circumferential direction. The bearing is surrounded by an intermediate element that rests against the bearing in the circumferential direction. The counter surfaces of the intermediate element are curved in such a manner that they register with and fit against the bearing. The intermediate element has three axially oriented slots that are spaced on the circumference so that the segments formed between the slots are radially slidable. The intermediate element is retained in a mount that tapers toward the threaded shaft so that the intermediate element is prevented from falling down. On the mount there is integrally formed a U-shaped retaining means for receiving a connection, compression or distraction rod. In the two retaining crosspieces of the retaining means there is provided an internal buttress thread into which a securing element for fixing the rod, which is implemented as a grub screw, is insertable. The intermediate element is thereby designed in such a manner that its upper region engages into the receiving slot of the retaining means. The term buttress thread is meant to include, besides the buttress metric thread DIN 513, buttress threads having a slightly larger or slightly smaller flank angle, a flank angle of 0° or a negative flank angle as well as buttress threads in accordance with EP 885 598.

Anchoring elements are also known from DE 39 23 996 C2, DE 100 05 385 A1, EP 1 090 595 A2 and WO 98/25534 A1 the pedicle screws of which comprise head ends in the shape of a spherical segment that are clampingly retained in a corresponding retaining means.

To implant said anchoring elements, the threaded shaft is first screwed into the corresponding vertebral body. Then, the rod is placed into the receiving slot and retained by a grub screw. As the grub screw is further tightened, the rod is pressed against the intermediate element so that the mount is displaced relative to the intermediate element. As the mount is configured to be tapered, the segments of the intermediate element are thereby pressed radially together and exert a retaining force onto the bearing. Put another way, in the released condition the mount with the retaining means is free to move with respect to the bearing or to the threaded shaft whilst in the tightened condition, the mount is fixedly and immovably retained on the bearing as a result of the clamping effect. The mount or retaining means may thereby be rotated about the longitudinal axis relative to the bearing and the mount or retaining means can be pivoted transverse the longitudinal axis according to the circular segment of the bearing. This makes it possible to first anchor the pedicle screw in the vertebral body and to then orient the retaining means in the desired manner in order to fix the rod in the optimum position with respect to the vertebral body.

In such-type anchoring elements, the retaining means is frictionally retained on the shaft. When utilizing said anchoring elements on the ventral vertebral column, the forces that are to be transmitted from the rod onto the vertebral body may be very large so that the frictional connection provided is not capable of transmitting these large forces. In such cases, the retaining means comes out of place and the rod is no longer in the desired position.

BRIEF SUMMERY OF THE INVENTION

In view thereof, it is the object of the present invention to provide an anchoring element of the type mentioned herein above that is capable, in spite of the retaining means being movably attached, of transmitting relatively large forces from the rod onto the vertebral body without sliding out of place.

An anchoring element configured according to the teachings of the present invention has the advantage that the mount and the retaining means are still movable with respect to the bearing and to the shaft and that the occurring forces are nevertheless positively transmitted thanks to the formed guiding surfaces and the mating counter surfaces. As compared to prior art, in this implementation the mount and the retaining means can only be moved in a direction transverse to the longitudinal axis. Therefore, the anchoring element of the invention could be called a uniaxial screw whereas the prior art anchoring element is termed a polyaxial screw since it is movable in any direction.

Another advantage of the anchoring element of the invention is that thanks to the positive force transmission the required clamping surface can be considerably reduced since it is no longer necessary to produce so strong a frictional connection. Therefore, the anchoring element of the invention can be implemented to be much smaller. This small anchoring element may then advantageously be implanted in the cervical vertebral region.

In a preferred embodiment, the guiding surfaces and/or the counter surfaces can be configured to be riffled or roughened. As a result thereof, the friction of the two surfaces against each other increases so that the forces required for fixing the mount or retaining means can be much smaller. Accordingly, this feature also contributes to reducing the size of the overall anchoring element since but a small surface is now needed to achieve sufficient clamping.

In another preferred embodiment a snap device is formed in the guiding surfaces and in the counter surfaces. Said snap device comprises, more specifically in the guiding surfaces and in the counter surfaces, radially disposed grooves that are spaced apart in such a manner that the counter surface engages into opposite grooves of the guiding surface and vice versa. During implementation, this registration fit of the two surfaces permits to already coarsely adjust the retaining means or the mount in the imposed snap steps prior to placing the rod. Prior to tightening the safety screw, fine adjustment is then of course still possible. This snap system facilitates implantation of the anchoring element and permits to further reduce its size since the retaining means or mount is already fixed by the snap system so that the actual clamping surface In a further preferred embodiment, the bearing is configured to be roughened, at least in its region which is in the shape of a spherical segment and/or in the retaining surfaces of the intermediate element that are turned toward said region. By having the bearing thus roughened, the clamping of the mount on the bearing is improved so that the clamping effect is enhanced while the surface remains the same.

Further advantages of the anchoring element of the invention will become apparent in the appended drawings and in the following description of embodiments thereof. Likewise, the above mentioned features and those described herein after may be used alone or in any combination with each other within the scope of the present invention. The embodiments discussed herein are merely exemplary in nature and are not intended to limit the scope of the invention in any manner.

BRIEF DESCRIPTION OF THE SEVERAL VIEWS OF THE DRAWING

In the drawing:

FIG. 1 is a front view of an anchoring element in accordance with the invention with an isolated securing element shown in an exploded view;

FIGS. 2a, 2b are sectional views of the anchoring element of FIG. 1, taken along the line II-II;

FIG. 3 is a top view of the anchoring element of FIG. 1, taken along the line III-III;

DETAILED DESCRIPTION OF THE INVENTION

Figure 4A:
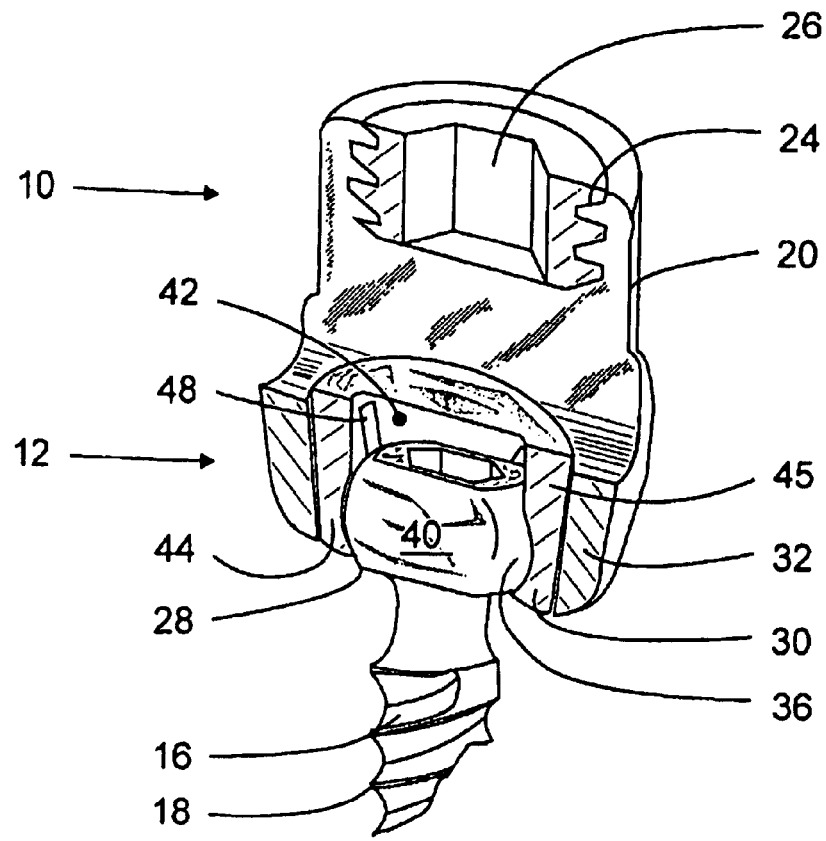
FIGS. 4a, 4b are partial perspective views of the anchoring elements according to FIGS. 2a and 2b.
Figure 4B:
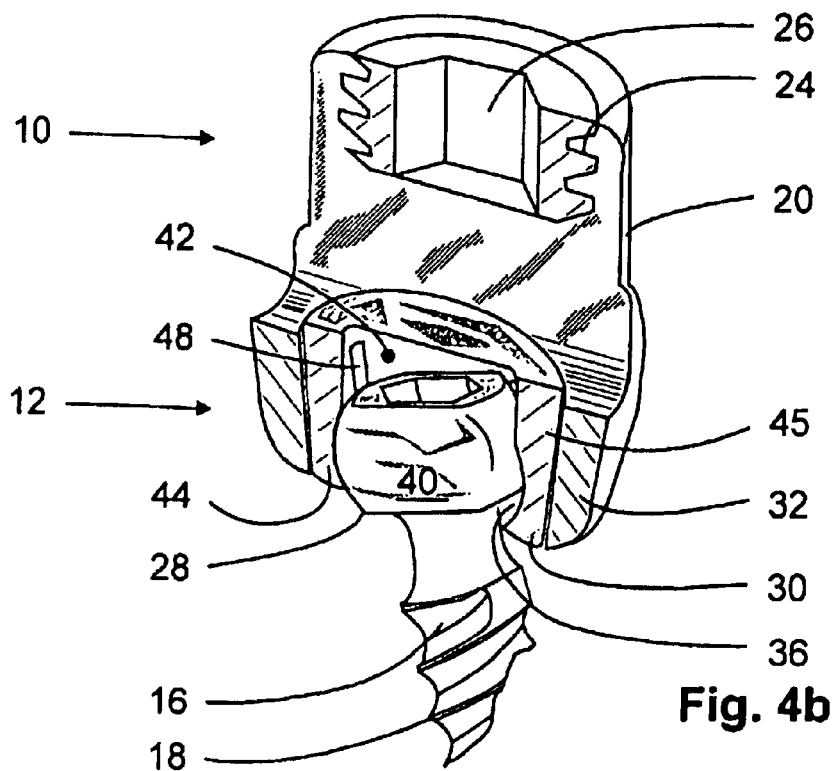
Figure 5:
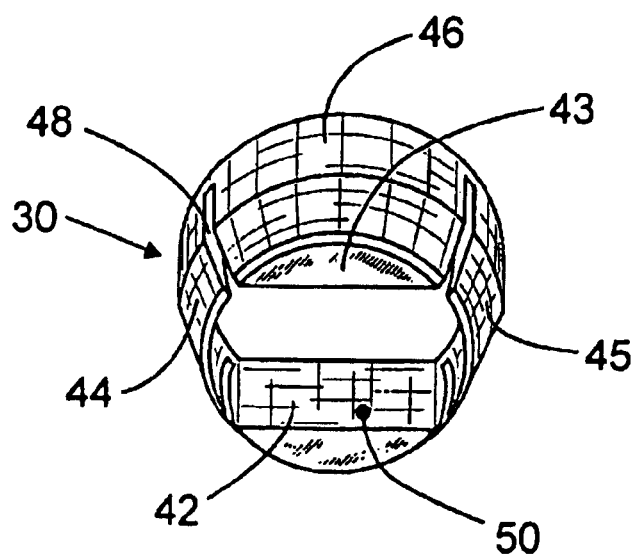
FIG. 5 is a perspective view of the intermediate element of the anchoring element of FIG. 1.
Figure 6:
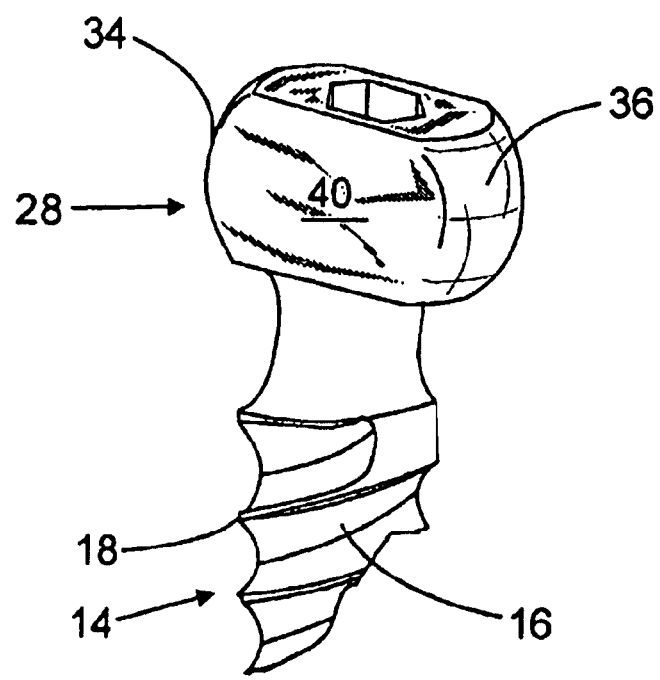
FIG. 6 is a perspective view of the bearing of the anchoring element of FIG. 1.

The anchoring element shown in the FIGS. 1 through 6 is a component part of a device for adjusting a human or animal vertebral column as it is sold for example by the trade name XIA available from Stryker Corp. This anchoring element serves to fasten a quite long rod on a vertebral bone and comprises a retaining means 10 for receiving a rod not shown herein, a clamping device 12 and a fastening element 14. The fastening element 14 is formed by a conically tapered shank 16 provided for example with a bio thread 18, a cancellous thread or the like. The anchoring element is inserted and fixed in the vertebral body by means of said fastening element 14.

The retaining means 10 is formed in a U-shaped configuration and comprises two coaxially arranged crosspieces 20, 22 provided, on their internal side, with a buttress thread 24. Said buttress thread 24 is described in detail in EP 0 885 598 A2. A securing element 26 configured as a grub screw may be screwed in axial direction into said retaining means 10 for fixing the rod inserted into said retaining means 10.

The clamping device 12 includes a bearing 28, integrally formed with the shank 16 and extending therefrom an axial prolongation of said shank, an intermediate element 30 surrounding the bearing 28 and a mount 32 encompassing the intermediate element 30. On two opposite sides 34, 36, the bearing 28 is configured as a spherical segment and is integrally formed with the shank 16. Two guiding surfaces 38, 40 having a plain configuration are provided between the sides 34, 36, said guiding surfaces being arranged so as to face each other as well.

In its region encompassing the bearing 28, the substantially ring-shaped intermediate element 30 is provided with two opposite flat segments 42, 43 and with two opposite curve segments 44, 45 that are held on a peripheral ring 46. A gap 48 is formed between the respective flat segments and curve segments 42, 43, 44, 45. The counter surfaces 50, 52 of the flat segments 42, 43 thereby abut flush against the plain guiding surfaces 38, 40, whereas the curve segments 44, 45 join and are flush with the sides 34, 36 having a shape of a fraction of a circle. Outwardly, the flat segments and the curve segments 42, 43, 44, 45 are circular and are received in the mount 32 with registration fit and yet with clearance. The mount 32 is in turn connected to, and integral with, the retaining means 10.

In its non-implanted state, the mount 32 may be rotated together with the retaining means 10 about the longitudinal axis of the anchoring element. At the same time, the mount 32, or the retaining means 10 respectively, may be pivoted parallel to the guiding surfaces 38, 40 and the counter surfaces 50, 52. In inserting the rod, which has not been illustrated herein, into the U-shaped retaining means 10, the rod comes to lie on the intermediate element extending into the U-shaped slot and is displaced relative to the mount 32, or the retaining means 10 respectively, by tightening the securing element 26 so that the intermediate element gets jammed between mount 32 and bearing 28, thus fixing the retaining means 10 on the shank 16. The anchoring element is hereby to be screwed into the vertebral bone in such a manner that the guiding surfaces 38, 40 be possibly arranged across the direction the rod is intended to be arranged in. As a result thereof, the forces originating from the rod may be optimally introduced into the shank 16 and into the vertebral bone by way of the guiding surfaces 38, 40.

In another embodiment not here presented, a grid is configured on the guiding surfaces 38, 40 and the mating counter surfaces 50, 52, radially oriented grooves being cut in each of the counter surfaces. The grooves of the one surface thereby receive the projections of the counter surface so that the guiding surfaces 38, 40 selectively mesh with the counter surfaces 50, 52. A snap device is thus realized by means of which the retaining means 10 may be pre-adjusted in any steps desired so that the actual mounting of the rod may be carried out quickly and without delay.

In another embodiment not here presented both the guiding surfaces 38, 40 and the counter surfaces 50, 52 are roughened in an effort to enhance the clamping effect.

The implantation of the anchoring element according to the invention and of the device for adjusting a human or animal vertebral column is performed as follows:

At first, the shank 16 is screwed, together with the bearing 28 arranged thereon, into the corresponding vertebral bone. It is thereby advisable to arrange the guiding surfaces 38, 40 across the direction the rod is intended to have at a later stage. Then, the retaining means 10 is roughly brought into the desired position prior to inserting the buttress thread 24 into the U-shaped retaining means 10 and to fixing it by means of the securing element 26. The securing element 26 thereby exerts a pressure onto the intermediate ring 30 and concurrently raises the mount 32 against the intermediate ring 30 so that the intermediate ring 30 gets jammed between retaining means 10 and bearing 28. In this position the clamping device permanently fixes the anchoring element while the forces emanating from the rod are introduced into the shank 16 and from there into the vertebral bone via the guiding surfaces 38, 40 and the counter surfaces 50, 52. In another preferred embodiment, the discrete surfaces are roughened, thus enhancing clamping.

In separating, in terms of force, the actual clamping force from the force to be transmitted, the surface needed to achieve clamping is considerably reduced so that the entire anchoring element may be realized in a much smaller size or, if the size is maintained, the forces that can be transmitted are accordingly larger. The smaller anchoring elements may then be inserted e.g., in the cervical vertebral region or at other locations that otherwise do not provide enough space.

LISTING OF NUMERALS

- 10 retaining means
- 12 clamping device
- 14 fastening element
- 16 shank
- 18 thread
- 20 crosspiece
- 22 crosspiece
- 24 buttress thread
- 26 securing element
- 28 bearing
- 30 intermediate element
- 32 mount
- 34 side
- 36 side
- 38 guiding surface
- 40 guiding surface
- 42 flat segment
- 43 flat segment
- 44 curve segment
- 45 curve segment
- 46 ring
- 48 gap
- 50 counter surface
- 52 counter surface

I claim:

1. An anchoring element for fastening a rod of a device for adjusting a human or animal vertebral column on a vertebra, said anchoring element having a retaining means (10) for receiving the rod, a securing element (26) that is attachable on the retaining means and acting against the rod, a fastening element (14) for attachment to the vertebral body and a clamping device (12) which is arranged between the retaining means (10) and the fastening element (14), including a ring-shaped mount (32), a bearing (28) and an intermediate element (30) embedded in the mount (32) and surrounding the bearing, said bearing (28) having the shape of a spherical segment on two opposing sides (34, 36) and comprising two guiding surfaces (38, 40) configured to be planar between the sides (34, 36) and also being oppositely disposed from each other, and said intermediate element (30) being substantially configured to be annular and comprising in its region surrounding the bearing (28) two opposing flat segments (42, 43) and two opposing curved segments (44, 45) so that the guiding surfaces (38, 40) abut onto counter surfaces (50, 52) formed on the flat segments (42, 43) so that the mount (32) is free to move toward the guiding surfaces (38, 40) relative to the bearing (28) when in its released state whilst the mount (32) is clampingly retained on the bearing (28) through the intermediate element (30) when in its clamped state characterized in that the counter surfaces (50,52) are formed on a respective one of the flat segments (42,43) of the intermediate element (30), said flat segments being disposed in the circumferential direction at a distance from curve segments (44,45) of the intermediate element (30) that are in the shape of a spherical segment.

2. The anchoring element as set forth in claim 1, characterized in that the mount (32) is rigidly connected to the retaining means (10) and the bearing (28) to the fastening element (14).

3. The anchoring element as set forth in claim 1, characterized in that the guiding surfaces and/or counter surfaces are configured to be riffled.

4. The anchoring element as set forth in claim 1, characterized in that the guiding surfaces and the counter surfaces comprise radially disposed grooves, said grooves being spaced apart in such a manner that the counter surface engages into opposite grooves of the guiding surface and vice versa.

5. The anchoring element as set forth in claim 1, characterized in that the guiding surfaces (30, 40) and/or counter surfaces (50, 52) are roughened.

6. The anchoring element as set forth in claim 1, characterized in that the bearing is configured to be roughened at least in its region which is in the shape of a spherical segment and/or in the retaining surfaces of the intermediate element that are turned toward said region.

* * * * *